United States Patent [19]
Slemker

[11] Patent Number: 5,888,217
[45] Date of Patent: *Mar. 30, 1999

[54] MODULAR INTERFACE CONNECTOR FOR A PROSTHETIC LIMB

[75] Inventor: Tracy C. Slemker, Clayton, Ohio

[73] Assignee: Materials Engineering And Development, Inc., Brookville, Ohio

[*] Notice: The term of this patent shall not extend beyond the expiration date of Pat. No. 5,662,715.

[21] Appl. No.: 781,381

[22] Filed: Jan. 11, 1997

Related U.S. Application Data

[63] Continuation of Ser. No. 504,320, Jul. 19, 1995, Pat. No. 5,662,715.

[51] Int. Cl.$^6$ .................................................. A61F 2/80
[52] U.S. Cl. ............................................ 623/36; 623/33
[58] Field of Search ........................................ 623/33–38

[56] References Cited

U.S. PATENT DOCUMENTS

| | | |
|---|---|---|
| 980,457 | 1/1911 | Toles . |
| 2,530,285 | 11/1950 | Catranis . |
| 2,533,404 | 12/1950 | Sharp et al. . |
| 2,671,225 | 3/1954 | Schoene et al. . |
| 2,696,011 | 12/1954 | Galdik . |
| 2,790,180 | 4/1957 | Hauser . |
| 2,808,593 | 10/1957 | Andersen . |
| 4,283,800 | 8/1981 | Wilson . |
| 5,133,777 | 7/1992 | Arbogast et al. ......................... 623/38 |
| 5,139,523 | 8/1992 | Paton et al. ............................. 623/37 |
| 5,139,524 | 8/1992 | Aulie et al. ............................. 623/38 |
| 5,163,965 | 11/1992 | Rasmusson et al. ..................... 623/36 |
| 5,263,990 | 11/1993 | Handal ..................................... 623/57 |
| 5,376,129 | 12/1994 | Faulkner et al. ......................... 623/33 |
| 5,443,526 | 8/1995 | Hoerner .................................. 623/28 |
| 5,507,837 | 4/1996 | Laghi ...................................... 623/28 |

FOREIGN PATENT DOCUMENTS

| | | |
|---|---|---|
| 2540138 | 10/1977 | Germany . |
| 2729800 | 4/1979 | Germany . |
| 305888 | 3/1970 | U.S.S.R. . |
| 311633 | 4/1970 | U.S.S.R. . |
| 465198 | 3/1975 | U.S.S.R. . |
| 1598999 | 7/1988 | U.S.S.R. . |
| 788563 | 7/1957 | United Kingdom . |
| 2087727 | 10/1980 | United Kingdom . |
| 2069847 | 2/1981 | United Kingdom . |
| 2169207 | 12/1985 | United Kingdom . |
| 8400881 | 3/1984 | WIPO . |

OTHER PUBLICATIONS

Enodolite literature "The Endolite Flexible Socket Valve". United States Manufacturing Co. literature "Super Seal Valve System".

*Primary Examiner*—David H. Willse
*Attorney, Agent, or Firm*—Thompson Hine & Flory LLP

[57] ABSTRACT

A modular interface connector for coupling a prosthetic limb socket assembly to a prosthetic limb upright assembly comprises an interface cushion member adapted to fit substantially entirely within the distal end of the socket, having a proximate end adapted to abut the wearer's residual limb; a first attachment mechanism for releasably attaching the interface connector within the distal end of the socket; and a second attachment mechanism for releasably attaching the upright assembly to the distal end of the socket. When attached in the socket, the interface connector provides an air-tight seal between the attachment mechanism and the wearer's residual limb.

13 Claims, 4 Drawing Sheets

MODULAR INTERFACE CONNECTOR FOR A PROSTHETIC LIMB

This is a continuation of application Ser. No. 08/504,320 filed Jul. 19, 1995, now U.S. Pat. No. 5,662,715.

BACKGROUND OF THE INVENTION

The present invention relates generally to prosthetic devices and, more particularly, to an interface connector for coupling prosthetic limb pylon or shaft components to a prosthetic limb socket component.

A prosthesis is often used to replace an amputated portion of a limb and to help restore the amputee's ability to use that limb. A prosthesis for a lower extremity amputation will often include an artificial foot connected to a upright assembly (pylon, tube or shaft) which is in turn connected to a custom fitted socket assembly (it is also known in the field to use non-custom fitted socket assemblies). If the amputation is an above-the-knee amputation, the upright assembly will commonly include an artificial knee joint.

An above-the-knee prosthesis typically requires two interlaying sockets; an inner socket consisting of a flexible, thermoplastic material, and a stronger, less flexible outer socket which is attached to the upright assembly of the prosthesis. The inner socket is typically designed to interface with and cushion the amputee's residual limb, to protect the amputee's residual limb from the interconnection components which attach the socket assembly to the upright assembly, and to provide an air-tight seal between the residual limb and the outer socket.

The outer socket is typically made from a hard thermoplastic material. The outer sockets can be created by heating a thermoplastic preform cone, stretching the heated cone over a positive cast of the amputee's residual limb, and then vacuum forming the cone in place over the positive cast. Alternatively, the outer socket can be fabricated by heating an extruded sheet of thermoplastic and wrapping the sheet over the positive cast; or by a laminating process using a fiber reinforced, thermal set plastic. Often times, interconnection components, such as an attachment plate, for coupling the outer socket to the upright assembly components of the prosthesis, will be permanently molded into the thermoplastic outer socket during the vacuum forming operation. Alternatively, the interconnection components may be permanently laminated into the socket.

Several disadvantages are inherent in these above-the-knee prosthetic devices. The combination of the inner socket, the interconnection components, and the outer socket give the prosthesis a long profile. Therefore, if the amputation is immediately above the knee, the prosthesis may extend the thigh beyond where the knee joint should be. Also, in preparing a positive cast for fabricating the outer socket, the thickness of the distal end of the positive cast is difficult to predict because the inner socket, the interconnection components, and the outer socket provide three levels of variance. This can lead to unpredictable dimensions in the socket assemblies. Furthermore, because the interconnection components are permanently attached into the socket assemblies, if a new socket is desired, the entire socket assembly including the interconnection components will have to be re-fabricated, and the socket and interconnection components of the old prosthesis will then be discarded.

Typically, a below-the-knee prosthesis will include an inner, soft insert material for interfacing with the amputee's residual limb, a set of interconnection components, and the outer socket. To fabricate the outer socket for this device a positive cast of the amputee's residual limb will be made, and then a layer of insert material, representing the thickness of the socket's inner insert material, will be formed over the cast. To account for the thickness of the interconnection components and to obtain proper alignment between the socket and the upright assembly, multiple layers of the insert material must be added to the distal end of the positive cast and then these layers must then be planed down to the precise angle and dimensions required. A disadvantage with this process is that it is very time consuming and requires much skill and equipment to accomplish.

Another disadvantage with typical below-the-knee prosthetic devices is that as the amputee's residual limb changes shape or size (as will often occur), the socket components will have to be replaced. Because the interconnection components are usually permanently molded into the sockets, the entire socket including the interconnection components will have to be re-fabricated, and the socket and interconnection components of the old prosthesis will then be discarded.

Accordingly, a need exists for improved prosthesis components which reduce the amount of skill, time, and equipment needed to fabricate or replace a prosthesis. A need exists for interface components which reduce the levels of variance in the socket fabrication processes. A need exists for interface components which reduce the longitudinal profile of the socket assemblies. Furthermore, a need exists for prosthesis components which facilitate the automation of the prosthesis fabricating process.

SUMMARY OF THE INVENTION

The present invention is an interface connector for a prosthetic limb which responds to the problems associated with the prior prosthetic limb devices. More particularly the present invention provides a modular interface connector for coupling the upright assemblies of the prosthesis to a single, plastic socket.

In accordance with the present invention, the modular interface connector for coupling a prosthetic limb socket to a prosthetic limb upright assembly comprises an interface cushion member adapted to abut the distal portion of an amputee's residual limb, and a base including means for releasably attaching the interface connector within the distal end of the socket and means for releasably attaching the prosthetic limb upright assembly to the distal end of the socket, where the cushion member is supported on the base.

In a preferred embodiment the interface cushion member has a substantially concave surface at its proximate end, adapted to abut the distal portion of an amputee's residual limb, and a flexible feathered periphery extending radially outwardly at the proximate end of the interface cushion member. The concave proximate surface and the feathered periphery of the interface cushion are provided such that the transition from the inner surface of the socket to the concave surface of the interface cushion is substantially smooth, and without wrinkles or creases.

In the same preferred embodiment, the interface cushion member also has a cavity in its distal end for mounting the base component therewithin. A lip extends inward from the rim of the cavity to secure the cushion to the base, and also provides an air-tight seal between the wearer's residual limb and the base component, when the interface connector is tightly fitted within the socket.

DETAILED DESCRIPTION

Figure 1:
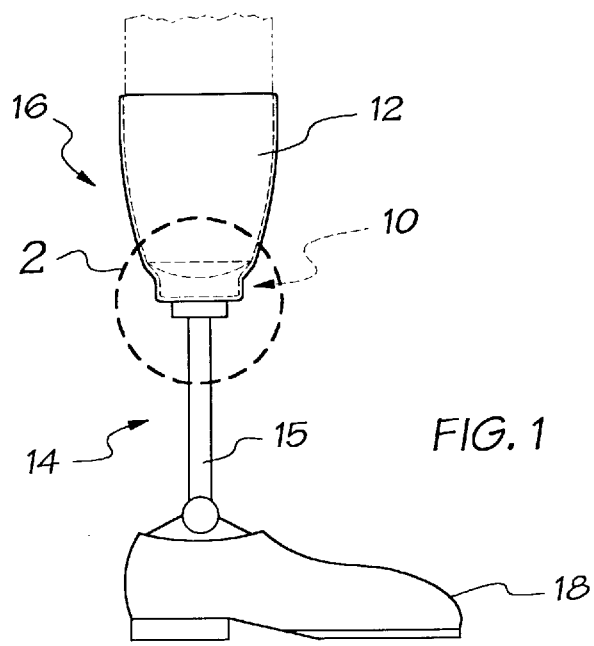
FIG. 1 is a prospective view of a lower extremity prosthesis incorporating the present invention.

As shown in FIG. 1 the modular interface connector of the present invention, generally depicted as 10, is used to connect a residual limb socket 12 to an upright assembly 14 of a prosthetic limb 16. In the present embodiment, the upright assembly 14 includes a pylon 15 which is in turn connected to an artificial foot 18.

Figure 2:
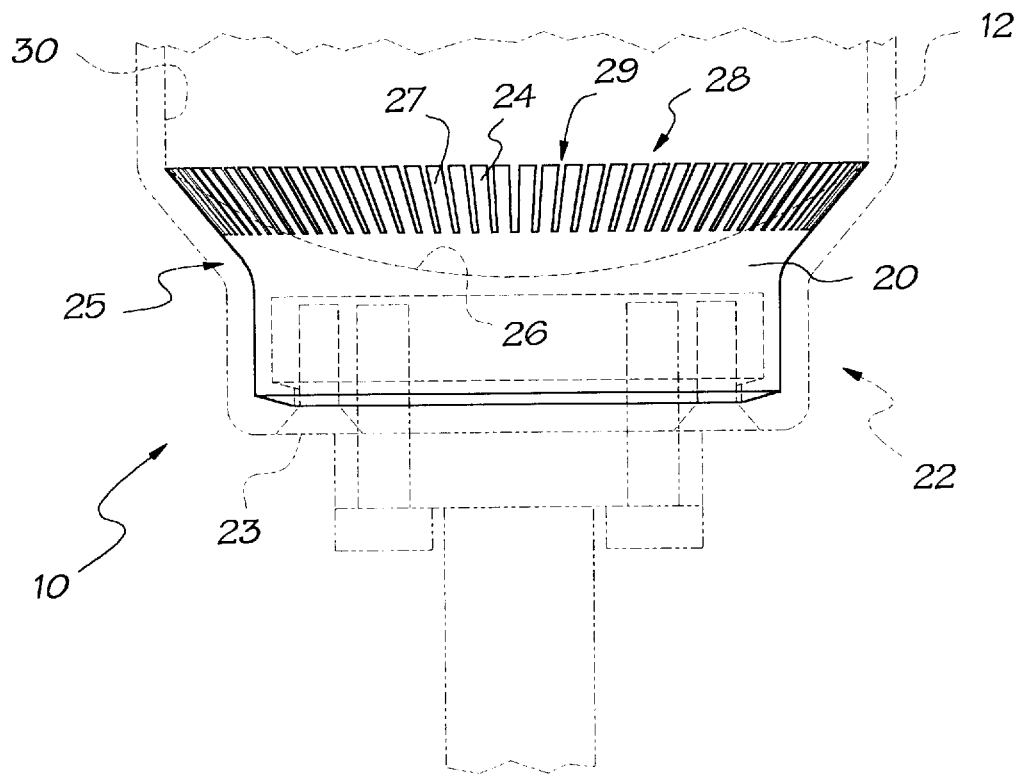
FIG. 2 is a close up cut away view of the area designated as 2 in FIG. 1.

As shown in FIG. 2 a first embodiment of the modular interface connector 10 has an interface cushion 20 which is shaped to fit within a distal socket extension 22 of the socket 12. The distal end 23 of the socket extension 22 is substantially flat. The interface cushion is preferably made from a thermoplastic polyurethane such as Santaprene (a registered trademark of Monsanto Corp.); although it is within the scope of the invention to construct the interface cushion from any elastomer material capable of providing the protection and sealing capabilities required by the invention as described below.

In a preferred embodiment, the interface cushion 20 has a multitude of tapered blades 24 extending from the outer periphery of the proximate end 25 of the interface cushion, giving the interface cushion a flexible feathered periphery 28 which conforms to the inner surface 30 of the socket 12 when the interface cushion is inserted into the socket extension 22. The proximate surfaces 27 of the blades are flush with the concave proximate surface 26 of the interface cushion. The feathered periphery 28 can also be described as a tapered annular flange extending from the outer periphery at the proximate end of the interface cushion, having a plurality of notches 29 circumferentially spaced about the flange.

The feathered periphery 28 further extends the concave surface 26 out to the inner surface 30 of the socket 12. The feathered periphery 28 allows the concave proximate surface 26 of the interface cushion 20 to smoothly transition into the inner surface 30 of the socket 12, substantially without the formation of creases or wrinkles.

Therefore, the cushioning provided by the interface cushion material, in combination with the concave proximate surface of the cushion and the smooth transition between the surfaces, allows for the amputee's residual limb to comfortably reside in the socket.

It is also within the scope of the invention that the interface cushion 20 have a tapered annular flange without notches.

Figure 3:
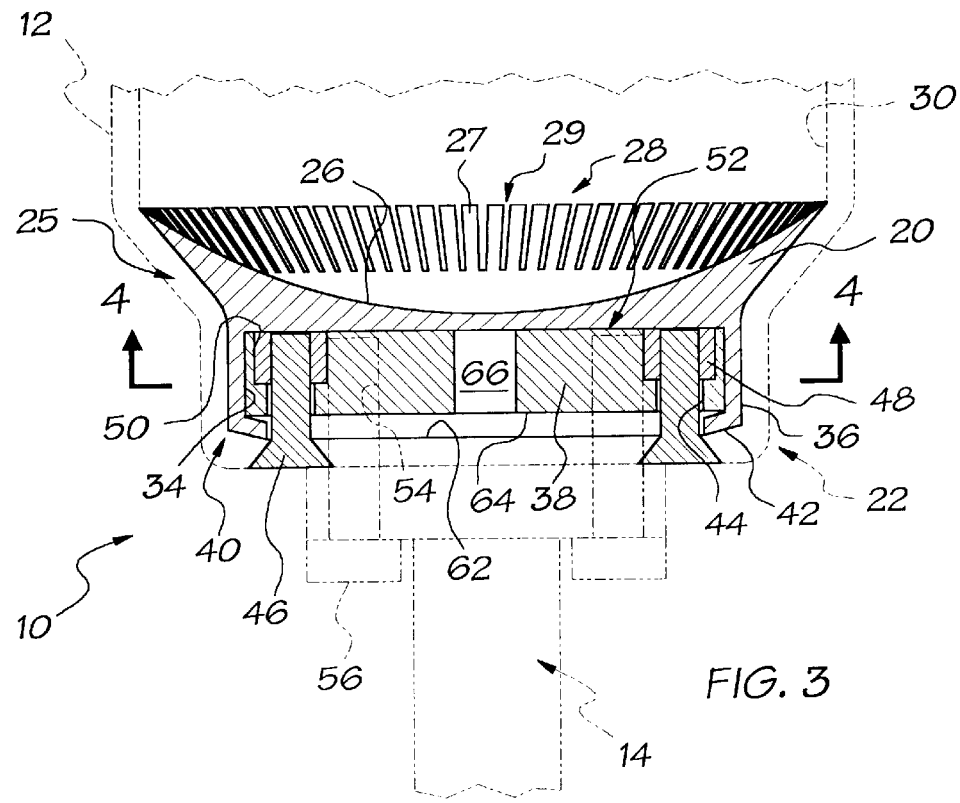
FIG. 3 is a cross-sectional view of the modular interface connector shown in FIG. 2.

As shown in FIG. 3, the interface cushion 20 has a cylindrical cavity 34 in its distal end 36 for mounting the interface cushion on a cylindrical base 38. The base 38 is held within the cavity 34 by an annular lip 42 extending radially inward from an outer rim 40 of the cavity. In a preferred embodiment, as will be described below, the annular lip 42 provides for an air-tight seal between the interconnection components (the base 38) and the amputee's residual limb (the proximate surface 26 of the interface cushion) when the interface connector is tightly fitted within the socket extension 22.

Figure 4:
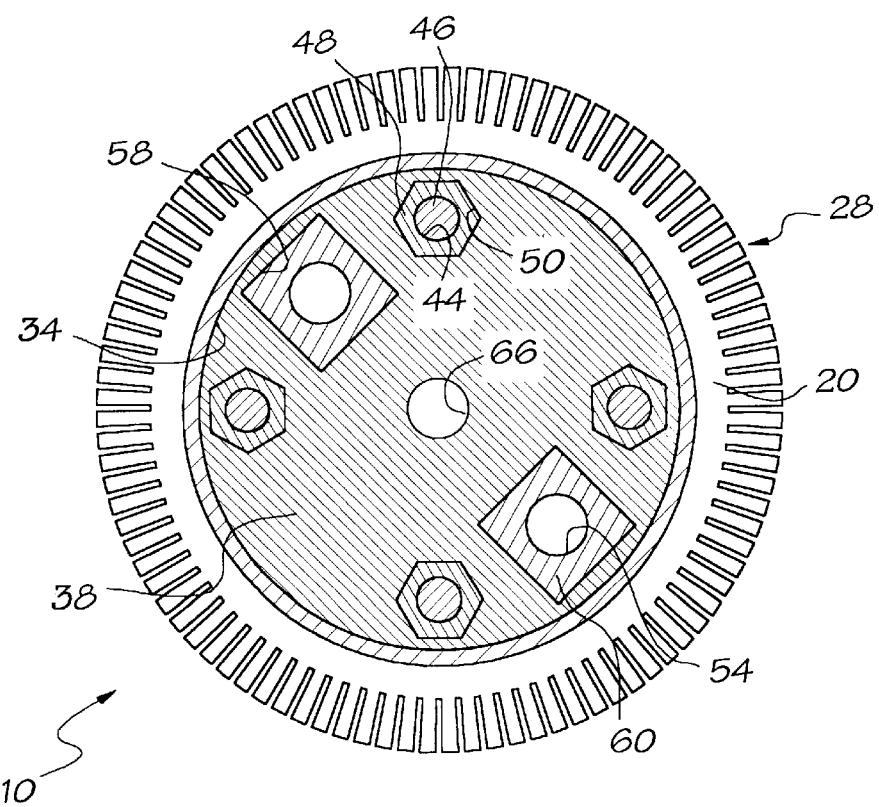
FIG. 4 is a cross-sectional view taken along lines 4—4 of FIG. 3.
Figure 5:
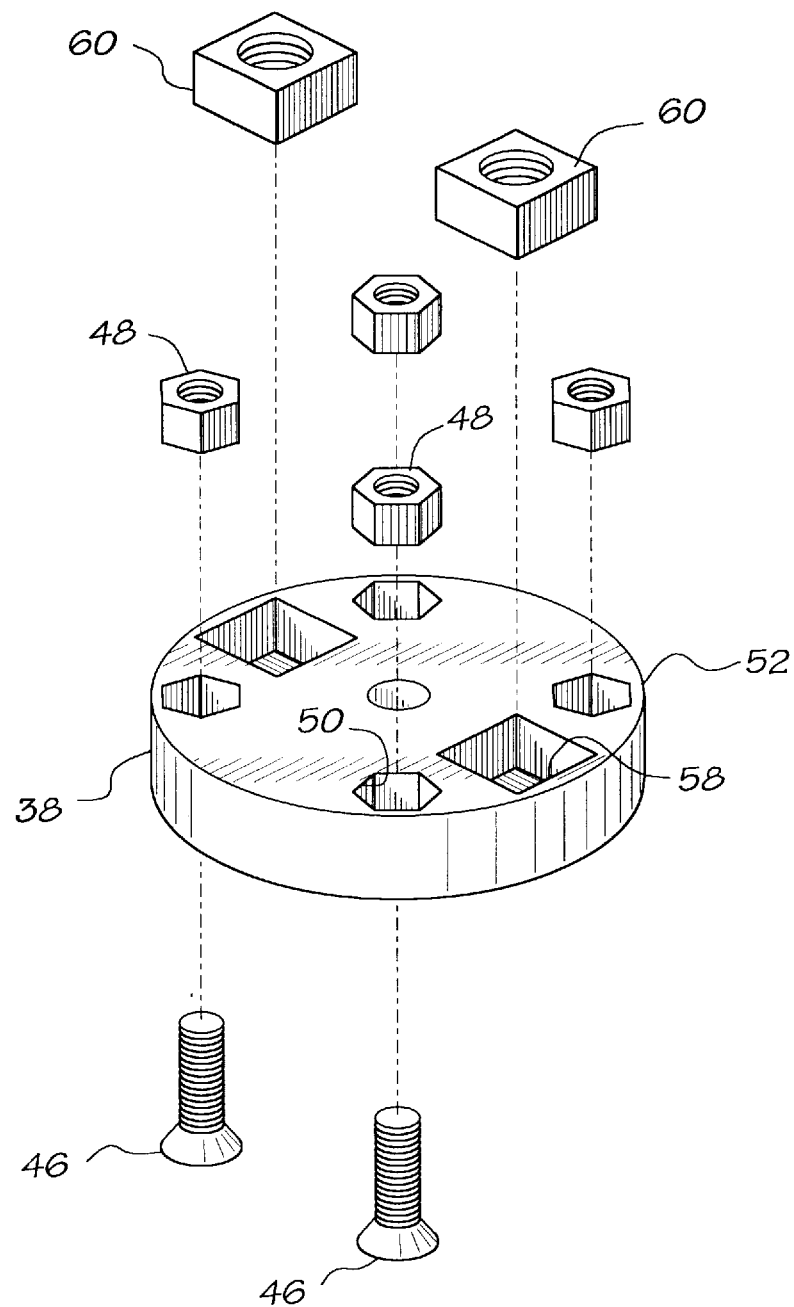
FIG. 5 is a prospective view of the coupling elements of the base of component of the present invention.

Referring to FIGS. 3–5 the base 38 has four holes 44 extending through for receiving attachment screws 46. Hex nuts 48 are inserted into hexagonal cutouts 50 in the proximate end 52 of the base. The cutouts 50 secure the hex nuts within the base, such that the screws 46 extending through holes (not shown) in the distal end of the socket 12 and into the holes 44 of the base 38 will releasably attach the modular interface connector 10 inside the socket extension 22.

Two additional holes 54 extend within the base 38 for receiving attachment bolts 56 used for attaching the upright assembly 14 to the socket 12. The base 38 has two square cutouts 58 in the proximate end 52 of the base for receiving square nuts 60 which are used to secure the bolts 56 within the base 38. The bolts 56 extend from the upright assembly 14, through holes (not shown) in the distal end of the socket 12 and into holes 54 of the base. Tightening the bolts 56 with respect to the square nuts 60 will attach the upright assembly 14 to the distal end of the socket 12. It is within the scope of the invention that the attachment bolts 56 and square nuts 60 can be used to attach the upright assembly 14 to the socket 12 and the modular interface connector 10 into the socket 12, without the need for additional attachment means. It is also within the scope of the invention that holes 44, 54 extending through the base 38 can be threaded such that the screws 46 and bolts 56 can be used to couple the prosthesis components together without the use of nuts 48, 60. It is also within the scope of the invention, that bolt shafts extend from the base 38, through the socket 12 and secured to the upright assembly 14 by the use of nuts, threaded holes or spring-lock assemblies commonly known in the art.

It is further within the scope of the invention that the interface connector 10 be either permanently or temporarily bonded into the socket. Furthermore, the interface connector may be retained in the socket by a suction device.

In the preferred embodiment, when the attachment screws 46 are tightened, attaching the rubber interface cushion 20 and base 38 of the modular interface connector 10 into the socket extension 22, the annular lip 42 is pressed between the inner surface 30 of the socket and the base 38, forming an air-tight seal between the proximate outer surface 26 and the base 38. This air-tight seal is provided such that suction is created in the socket when the residual limb is inserted into the socket. This holds the prosthesis on the residual limb. The seal also protects the interconnection components from the amputee's perspiration.

The portion 62 of the socket inner surface 30 at the flat distal end 23 of the socket extension 22 is preferably perfectly parallel to the distal surface 64 of the base 38. This helps to prevent the screws 46 and bolts 56 from breaking, and helps prevent cold-flow damage of the socket 12. Guide-hole 66, positioned at the exact center of the base, facilitates the precise positioning of the holes 44, 54 used for coupling the base to the socket, and used for coupling the pylon components to the base.

Because screws, bolts and nuts are preferably used to attach the modular interface connector 10 within the socket 12, the interface connector 10 can be easily removed from the socket and inserted into a new socket if necessary, without damaging the interface connector or socket.

A general procedure for fabricating the socket 12 for use with the present invention is as follows. A positive cast of the amputee's residual limb is first made by one of many known procedures. This positive cast will be used as a mold for the socket. The positive cast, therefore, is further sculpted (built-up or chiseled away) according to known biomechanical considerations, i.e., for a below the knee socket, the socket should be tighter around the knee and extended near the bottom. To assist in these modifications, during the positive cast fabrication process, several bony points of the residual limb will be "landmarked" on the positive cast.

Before fabrication of the socket, a fabricating plate having the same dimensions of the interface cushion 20 is attached to the distal end of the positive cast to provide for the socket extension 22. If the interface connector 10 is standardized, the same fabricating plate can be used in the fabrication of every socket.

After the fabricating plate has been fastened to the cast, a thermoplastic preform cone is heated and stretched over the positive cast. The cone is then sealed around the base of the cast and a vacuum is applied between the cone and the cast to create an intimate fit of the cone over the cast. When hardened, the cone is removed from the cast, and the result is a hard plastic socket 12 having an extended portion 22 shaped to receive the interface connector 10. Holes are then formed in the distal end of the socket to facilitate the attachment screws 46 and bolts 56.

The above socket fabricating process may also be entirely automated. A digitizing device will first create a three-dimensional digital image (digital dimensions) of the amputee's residual limb. This digital image may include the outer surface dimensions of the residual limb, and may also include internal bone structure and muscle structure dimensions depending upon the complexity of the digitizing device used. This digital image will be then fed into a computer-aided design ("CAD") system, where a knowledge-based computer program running on the CAD will generate the digital dimensions of the socket based upon the image of the residual limb. This program will add the necessary biomechanical modifications to the socket's digital. dimensions, and will also incorporate the dimensions of the universal interface connector 10 to form the socket extension 22. The modified socket dimensions are then sent to a CNC machine which "squirt-shapes" the plastic socket according to the dimensions. The modified dimensions may alternatively be sent to a CNC lathe machine to carve a positive mold (similar to the positive cast discussed above) to be used in vacuum forming the socket from a preform cone as described above.

Once the socket has been fabricated, the interface connector 10 is inserted into the socket extension 22, and tightly fitted therein by screws 46 or other attachment means as described above. The upright assembly 14 of the prosthetic limb is then attached to the socket 12 and interface connector 10 by bolts 56 or other attachment means as described above. Because the interface connector 10 can be universal (i.e., the interface connector is standardized and can be interchangeably used in the fabrication of virtually every prosthetic limb of similar application), only the socket component 12 of the prosthetic limb may need to be custom sized, fit, and fabricated; and this socket can be more precisely constructed due to the reduced levels of variance provided by the interface connector. It is also within the scope of the invention that the interface connector 10 be used with a socket that does not require custom fitting.

Figure 6:
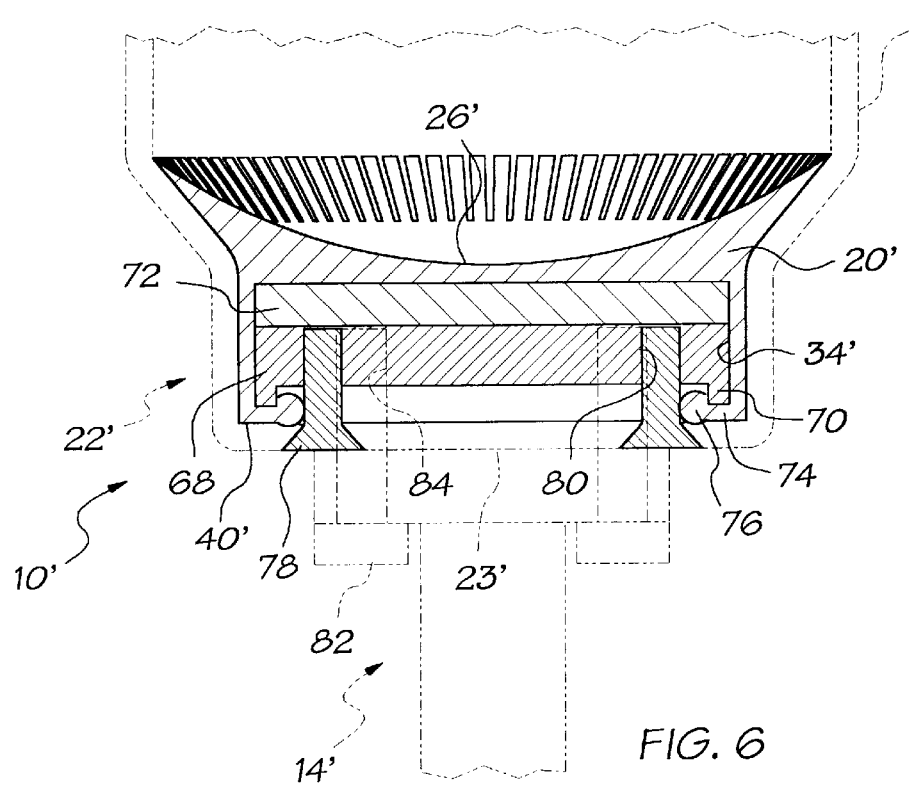
FIG. 6 is a cross-sectional view of a second embodiment of the invention.

As shown in FIG. 6, a second embodiment of the interface connector 10' has a cylindrically shaped metal base 68 with an annular rim 70 extending distally from the periphery of the base. The base 68 is mounted within a cylindrical cavity 34' of the interface cushion 20'. A removable porous pad 72, interposed between the base 68 and the interface cushion 20' in the cavity 34', provides additional cushioning for the wearer's residual limb. An annular shoulder 74 extends radially inward from the outer rim 40' of the cavity 34', and projects over the annular rim 70 to retain the base 68 and pad 72 within the cavity 34'. An annular o-ring projection 76 extends radially inward from the shoulder 74 and engages the rim 70 to form an air-tight seal between the base 68 and the proximate surface 26' of the interface cushion when the interface cushion is tightly fitted within the socket extension 22'.

The interface connector 10' is releasably attached in the socket extension 22' by four screws 78 extending through holes in the distal end of the socket and engaged by threaded holes 80 in the base 68. The upright assembly 14' is releasably attached to the distal end 23' of the socket by two bolts 82 extending from the upright assembly, through holes in the distal end of the socket and engaged by threaded holes 84 in the base 68.

Figure 7:
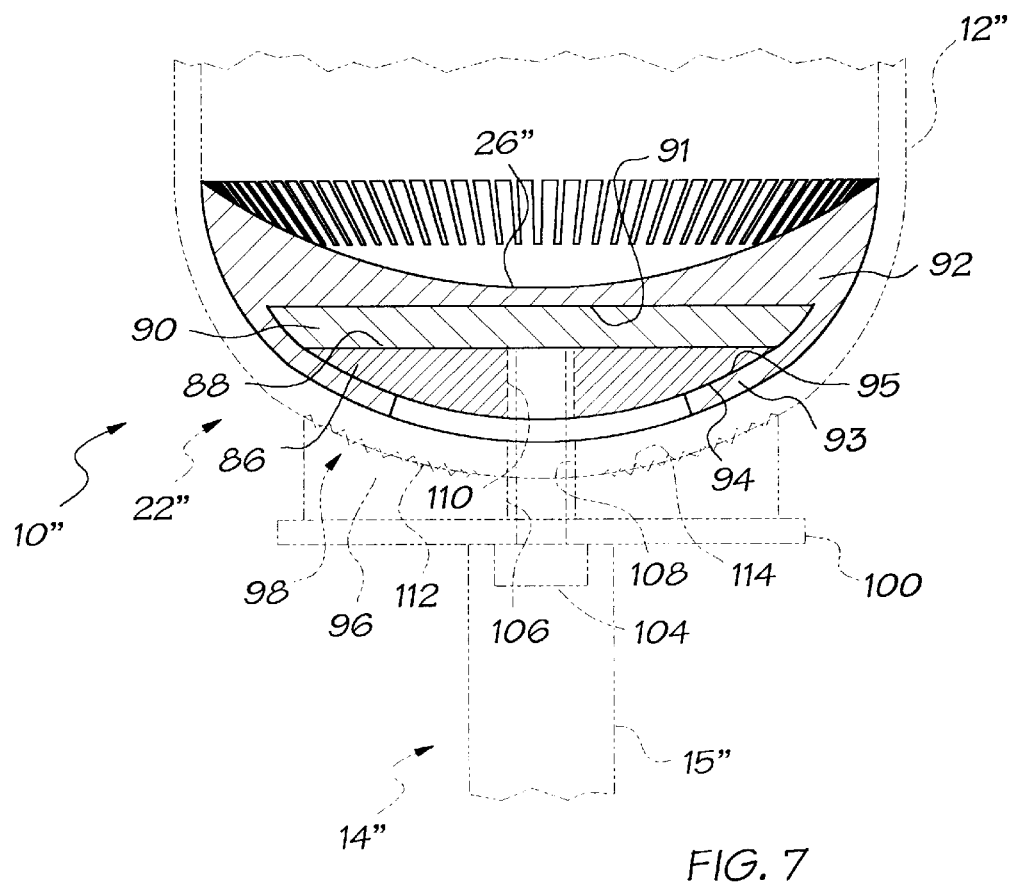
FIG. 7 is a cross-sectional view of a third embodiment of the invention.

As shown in FIG. 7, third embodiment of the interface connector 10" has a hemispherical shaped base 86 with its flat surface 88, abutting the distal end of a removable porous pad 90 which is interposed between the base 86 and a distal flat surface 91 of a substantially hemispherical interface cushion 92. An annular flange 93 extends radially inward from the periphery of the flat surface 91, partially over the domed distal surface 94 of the base 86. The flange 93 secures the base 86 and pad 90 within a domed cavity 95 formed by the flange 93, and also provides an air-tight seal between the proximate surface 26" of the interface connector and the base 86 when the interface connector is tightly fitted within the socket extension 22".

The upright assembly 14" of the this embodiment comprises a cup-shaped seat 96 for receiving the domed distal end 98 of the socket extension 22". The upright assembly further comprises a plate 100 and a pylon 15". A bolt 104 is used to simultaneously attach the upright assembly 14" to the distal end 98 of the socket extension 22" and attach the interface connector 10" within the socket extension 22". The bolt 104 extends from the plate 100, through a hole 106 in the seat 96, through a hole 108 in the socket, and into a hole 110 in the base 86. The bolt 104 is secured into the base 86 by either a nut (not shown) or by threads in the hole 110. The holes in the seat and socket 106, 108 are preferably oversized to facilitate the angular adjustment of the upright assembly 14" with respect to the socket 12". The outer domed surface 112 of the distal end 98 of the socket extension 22" abuts the concave outer surface 114 of the seat 96. Both surfaces 112, 114 are textured such that they restrict movement of the socket 12" and the seat 96, with respect to each other, when the bolt 104 is tightly secured in the base 86.

Having described the invention in detail and by reference to the drawings, it will be apparent that modification and variations are possible without departing from the scope of the invention as defined in the following claims.

What is claimed is:

1. A prosthetic limb, comprising:
    a plastic socket cone formed according to dimensions of a wearer's residual limb, said socket cone having a socket interior, an inner surface, and a distal end;
    an upright assembly releasably mounted to said distal end of said socket cone; and
    a substantially disc-shaped, modular interface coupling releasably mounted within said socket interior against said inner surface of said socket cone at said distal end of said socket cone;

said modular interface coupling having a distal end and including at least one screw- or bolt-receiving hole extending into its distal end;

said socket cone including a hole extending through its distal end and aligned with said screw- or bolt-receiving hole of said modular interface coupling;

said upright assembly includes a threaded screw or bolt extending proximally therefrom, through said hole of said socket cone and into said screw- or bolt-receiving hole of said modular interface coupling;

said modular interface coupling including a threaded means for engaging said threaded screw or bolt of said upright assembly extending into said screw- or bolt-receiving hole of said modular interface coupling; and the prosthetic limb further comprising a substantially annular, elastomeric projection extending therefrom, encircling said screw- or bolt-receiving hole and extending between said distal end of said modular interface coupling and said inner surface of said socket cone at said distal end of said socket cone;

whereby, as said threaded screw or bolt is tightened within said threaded means of said modular interface coupling, said annular projection is pressed between said distal end of said modular interface coupling and said inner surface of said socket cone at said distal end of said socket cone, forming an air-tight seal between said modular interface coupling and said inner surface of said socket cone, and simultaneously mounting said upright assembly to said distal end of said socket cone.

2. The prosthetic limb of claim 1, further comprising a cushion member carried on a proximate end of said modular interface coupling, said cushion member having a concave proximate end, whereby said cushion member provides comfort to a wearer's residual limb when the prosthetic limb is worn on the wearer's residual limb.

3. The prosthetic limb of claim 2, wherein said cushion member extends about said circumference of said modular interface coupling and includes said substantially annular elastomeric projection.

4. The prosthetic limb of claim 1, wherein:

said inner surface of said socket cone is substantially flat at said distal end of said socket cone;

said modular interface coupling includes a substantially flat distal surface; and said flat distal surface of said modular interface coupling is positioned substantially parallel to said substantially flat inner surface at said distal end of said socket cone.

5. An interface connector for coupling a prosthetic limb socket to a prosthetic limb upright assembly, the socket being fabricated according to dimensions of a wearer's residual limb, and having a socket interior, an inner surface and a distal end, the interface connector comprising:

a base adapted to fit substantially entirely within the socket interior at the distal end of the socket, said base having a proximate end;

an interface cushion member mounted on said proximate end of said base, said interface cushion member having a proximate end and a distal end, said proximate end of said interface cushion member being adapted to abut and provide comfort to a wearer's residual limb, said interface cushion member including a cavity opening onto said distal end of said interface cushion member, said base being retained within said cavity by a projection extending from a mouth of said cavity;

a first attachment mechanism, carried on said base, adapted to releasably attach said base within the socket interior at the distal end of the socket; and second attachment mechanism, carried on said base, adapted to releasably attach the prosthetic limb upright assembly to the distal end of the socket, said first and second attachment mechanisms being the same or different;

said projection being adapted to abut the inner surface of the socket and to provide an air-tight seal between said second attachment mechanism and the interior of the socket when said base is attached within the socket interior at the distal end of the socket by said first attachment mechanism.

6. The interface connector of claim 5, wherein said projection is an o-ring.

7. An interface connector for coupling a prosthetic limb socket to a prosthetic limb upright assembly, the socket being fabricated according to dimensions of a wearer's residual limb, and having a socket interior, an inner surface and a distal end, the interface connector comprising:

a base adapted to fit substantially entirely within the socket interior at the distal end of the socket, said base having a proximate end;

an interface cushion member mounted on said proximate end of said base, said interface cushion member having a proximate end and a distal end, said proximate end of said interface cushion member being adapted to abut and provide comfort to a wearer's residual limb, said interface cushion member including a cavity opening onto said distal end of said interface cushion member, said base being retained within said cavity by a projection extending from a mouth of said cavity;

a first attachment mechanism, carried on said base, adapted to releasably attach said base within the socket interior at the distal end of the socket; and a second attachment mechanism, carried on said base, adapted to releasably attach the prosthetic limb upright assembly to the distal end of the socket, said first and second attachment mechanisms being the same or different;

said base being substantially cylindrical;

said interface cushion member including a substantially cylindrical body, a substantially concave proximate surface, and a tapered flange extending radially outward from said concave proximate surface; and said cavity extending into said cylindrical body of said interface cushion member.

8. The interface connector of claim 7, wherein said flange includes a plurality of circumferentially spaced notches, said notches being adapted to provide a smooth transition from the inner surface of the socket to the concave proximate surface of the interface cushion member, substantially without wrinkles or creases, when said base is attached within the socket interior at the distal end of the socket by said first attachment mechanism.

9. An interface connector for coupling a prosthetic limb socket to a prosthetic limb upright assembly, the socket being fabricated according to dimensions of a wearer's residual limb, and having a socket interior, an inner surface and a distal end, the interface connector comprising:

a base adapted to fit substantially entirely within the socket interior at the distal end of the socket, said base having a proximate end;

an interface cushion member mounted on said proximate end of said base, said interface cushion member having a proximate end and a distal end, said proximate end of said interface cushion member being adapted to abut and provide comfort to a wearer's residual limb, said interface cushion member including a cavity opening onto said distal end of said interface cushion member, said base being retained within said cavity by a projection extending from a mouth of said cavity;

a first attachment mechanism, carried on said base, adapted to releasably attach said base within the socket interior at the distal end of the socket, said first attachment mechanism including at least one bolt-receiving bore extending into a distal end of said base; and a second attachment mechanism, carried on said base, adapted to releasably attach the prosthetic limb upright assembly to the distal end of the socket, said second attachment mechanism including at least one bolt-receiving bore extending into said distal end of said base, said first and second attachment mechanisms being the same or different.

10. An interface connector for coupling a prosthetic limb socket to a prosthetic limb upright assembly, the socket being fabricated according to dimensions of a wearer's residual limb, and having a socket interior, an inner surface and a distal end, the interface connector comprising:

base adapted to fit substantially entirely within the socket interior at the distal end of the socket, said base having a proximate end;

an interface cushion member mounted on said proximate end of said base, said interface cushion member having a proximate end and a distal end, said proximate end of said interface cushion member being adapted to abut and provide comfort to a wearer's residual limb, said interface cushion member including a cavity opening onto said distal end of said interface cushion member, said base being retained within said cavity by a projection extending from a mouth of said cavity;

a first attachment mechanism, carried on said base, adapted to releasably attach said base within the socket interior at the distal end of the socket; and a second attachment mechanism, carried on said base, adapted to releasably attach the prosthetic limb upright assembly to the distal end of the socket, said first and second attachment mechanisms being the same or different;

said base being substantially cylindrical and including an annular rim extending distally from a distal end of said base;

said interface cushion member including a substantially cylindrical body into which said cavity extends, a substantially concave proximate surface, a tapered flange extending radially outward from said concave proximate surface, and an annular shoulder extending radially inward over said annular rim; and said projection being an o-ring extending radially inward from said shoulder and engaging said rim.

11. The interface connector of claim 10, further comprising a porous pad positioned in said cavity between said base and said cushion member, said pad adapted to provide additional cushioning for a wearer's residual limb.

12. An interface connector for coupling a prosthetic limb socket to a prosthetic limb upright assembly, the socket being fabricated according to dimensions of a wearer's residual limb, and having a socket interior, an inner surface and a distal end, the interface connector comprising:

a base adapted to fit substantially entirely within the socket interior at the distal end of the socket, said base having a proximate end;

an interface cushion member mounted on said proximate end of said base, said interface cushion member having a proximate end and a distal end, said proximate end of said interface cushion member being adapted to abut and provide comfort to a wearer's residual limb, said interface cushion member including a cavity opening onto said distal end of said interface cushion member, said base being retained within said cavity by a projection extending from a mouth of said cavity;

a first attachment mechanism, carried on said base, adapted to releasably attach said base within the socket interior at the distal end of the socket; and a second attachment mechanism, carried on said base, adapted to releasably attach the prosthetic limb upright assembly to the distal end of the socket, said first and second attachment mechanisms being the same or different;

said base being substantially hemispherical, having a substantially flat proximal surface and a domed distal surface; and said interface cushion member including a substantially hemispherical body into which said cavity extends, a substantially concave proximate surface, and a tapered flange extending radially from said concave proximate surface.

13. The interface connector of claim 12, wherein said first and second attachment mechanisms include a bolt-receiving bore extending through a distal end of said base.

* * * * *

UNITED STATES PATENT AND TRADEMARK OFFICE
CERTIFICATE OF CORRECTION

PATENT NO.   : 5,888,217
DATED        : MARCH 30, 1999
INVENTOR(S)  : TRACY C. SLEMKER

It is certified that error appears in the above-indentified patent and that said Letters Patent is hereby corrected as shown below:

Claim 1, Col. 7, Line 18 - Words "extending therefrom" to be deleted

Claim 1, Col. 7, Line 19 - A --,-- is missing after "hole".

Claim 3, Col. 7, Line 39 - Word "said" first occurrence, should be replaced with --a--

Claim 5, Col. 8, Line 4 - Word --a-- is missing before word "second".

Claim 9, Col. 9, Line 12 - Word "said" first occurrence, should be replaced with --a--

Claim 10, Col. 9, Line 25 - Word --a-- is missing before word "base".

Signed and Sealed this

Fourteenth Day of September, 1999

Q. TODD DICKINSON

Attest:

Attesting Officer

Acting Commissioner of Patents and Trademarks